United States Patent
Curiel et al.

(10) Patent No.: US 10,226,311 B2
(45) Date of Patent: *Mar. 12, 2019

(54) CLIP-BASE-BRACKET ASSEMBLY HAVING A BASE FOR AN ORTHODONTIC APPARATUS AND ORTHODONTIC APPARATUS COMPRISING SAME

(71) Applicant: American Orthodontics Corporation, Sheboygan, WI (US)

(72) Inventors: Patrick Curiel, Neuilly sur Seine (FR); Philippe Salah, Paris (FR); William Ayache, Neuilly sur Seine (FR)

(73) Assignee: American Orthodontics Corporation, Sheboygan, WI (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/160,555

(22) Filed: May 20, 2016

(65) Prior Publication Data

US 2016/0262851 A1 Sep. 15, 2016

Related U.S. Application Data

(63) Continuation of application No. 13/997,555, filed as application No. PCT/EP2011/074068 on Dec. 27, 2011, now Pat. No. 9,393,084.

(30) Foreign Application Priority Data

Dec. 28, 2010 (FR) ...................................... 10 61306

(51) Int. Cl.
*A61C 7/30* (2006.01)
*A61C 7/28* (2006.01)

(52) U.S. Cl.
CPC .............. *A61C 7/285* (2013.01); *A61C 7/287* (2013.01); *A61C 7/30* (2013.01)

(58) Field of Classification Search
CPC ............ A61C 7/30; A61C 7/285; A61C 7/287
See application file for complete search history.

(56) References Cited

U.S. PATENT DOCUMENTS

| 4,248,588 A | 2/1981 | Hanson |
| 4,419,078 A | 12/1983 | Pletcher |
| (Continued) | | |

FOREIGN PATENT DOCUMENTS

| DE | 1407100 A1 | 9/1995 |
| EP | 1234549 A1 | 8/2002 |
| (Continued) | | |

OTHER PUBLICATIONS

International Search Report, PCT International Application No. PCT/EP2011/074068, dated Mar. 5, 2012.

(Continued)

*Primary Examiner* — Ralph Lewis
(74) *Attorney, Agent, or Firm* — Andrus Intellectual Property Law, LLP

(57) ABSTRACT

A self-ligating attachment intended to form part of an orthodontic appliance, the external surface of said attachment being provided with a groove for receiving an orthodontic arch. A elastic clip that can be reversibly moved between an open position forming an open passage allowing the insertion of the arch into the groove and a closed position sealing the groove. A base including an external surface that supports the attachment and an occlusal surface which is intended to rest on one of the patient's teeth, so as to hug the surface of the tooth. In addition, the base comprises a support for the attachment and said base assists in the guiding of the clip, cooperating with the attachment, as the clip moves between the open and closed positions.

19 Claims, 9 Drawing Sheets

(56) References Cited

U.S. PATENT DOCUMENTS

| | | | |
|---|---|---|---|
| 4,496,318 A * | 1/1985 | Connelly, Jr. ......... | A61C 7/282 433/14 |
| 5,474,445 A | 12/1995 | Voudouris | |
| 5,562,444 A | 10/1996 | Heiser et al. | |
| 5,630,715 A | 5/1997 | Voudouris | |
| 5,711,666 A | 1/1998 | Hanson | |
| 5,857,850 A | 1/1999 | Voudouris | |
| 5,906,486 A | 5/1999 | Hanson | |
| 5,913,680 A | 6/1999 | Voudouris | |
| 6,071,118 A | 6/2000 | Damon | |
| 6,071,119 A | 6/2000 | Christoff | |
| 6,168,428 B1 | 1/2001 | Voudouris | |
| 6,257,883 B1 | 7/2001 | Voudouris | |
| 6,368,105 B1 | 4/2002 | Voudouris et al. | |
| 6,939,133 B2 | 9/2005 | Voudouris | |
| 7,104,791 B2 * | 9/2006 | Hanson ................. | A61C 7/145 433/10 |
| 7,214,057 B2 | 5/2007 | Voudouris | |
| 7,247,019 B2 | 7/2007 | Abels et al. | |
| 7,416,408 B2 | 8/2008 | Farzin-Nia et al. | |
| 7,442,039 B2 | 10/2008 | Opin et al. | |
| 7,611,353 B2 | 11/2009 | Sommer | |
| 7,963,767 B2 | 6/2011 | Lewis et al. | |
| 9,393,084 B2 * | 7/2016 | Curiel ................... | A61C 7/285 |
| 2004/0166459 A1 | 8/2004 | Voudouris | |
| 2004/0175667 A1 | 9/2004 | Abels et al. | |
| 2007/0072143 A1 | 3/2007 | Sommer | |
| 2007/0166658 A1 | 7/2007 | Voudouris | |
| 2009/0004617 A1 | 1/2009 | Oda et al. | |
| 2010/0261131 A1 | 10/2010 | Ruiz-Vela et al. | |

FOREIGN PATENT DOCUMENTS

| | | |
|---|---|---|
| EP | 1287789 A2 | 3/2003 |
| WO | 2008044912 A1 | 4/2008 |
| WO | 2010028276 A1 | 3/2010 |
| WO | 2010103178 A1 | 9/2010 |

OTHER PUBLICATIONS

Office Action and Machine Translation in corresponding European Patent Application No. 11807941.7, dated Mar. 31, 2017.

* cited by examiner

CLIP-BASE-BRACKET ASSEMBLY HAVING A BASE FOR AN ORTHODONTIC APPARATUS AND ORTHODONTIC APPARATUS COMPRISING SAME

CROSS-REFERENCE TO RELATED APPLICATIONS

This application is a continuation of U.S. application Ser. No. 13/997,555 filed Sep. 3, 2013 which application published on Dec. 19, 2013 as U.S. Publication No. 2013/0337397, which application is a U.S. national stage application of International Application PCT/EP2011/074068, filed Dec. 27, 2011, which international application was published on Jul. 5, 2012, as International Publication WO 2012/089720 in the French language. The International Application claims priority of French Patent Application 1061306, filed Dec. 28, 2010.

The invention relates to a base/bracket assembly to be used in a customized orthodontic apparatus for treating a patient and intended mainly, but not exclusively, to be used in the case of a lingual technique, that is to say with the apparatus located on the non-visible posterior face of the teeth.

Conventionally, such apparatuses comprise:
at least one orthodontic arch wire, in other words a metal wire which exerts on the teeth a force that tends to move them from their unsatisfactory initial position, known as the "malposition", into a satisfactory final position, known as the "corrected position";
and a set of brackets which are each provided with at least one groove for holding an orthodontic arch wire.

The brackets are fixed individually to the patient's teeth in a predetermined position that allows the orthodontic arch wire to transfer to the teeth the necessary forces for them to pass from the malposition into the corrected position during the treatment. This fixing is produced by way of a "base", that is to say an intermediate element, one face of which conforms to the surface of the tooth to which the bracket is intended to be fixed, and the other face of which supports the bracket.

Most commonly, one or more orthodontic arch wires, together with a single set of brackets each comprising one or more grooves, are used.

The development of lingual orthodontic techniques, which have the esthetic advantage of leaving the apparatus virtually invisible from the outside, started around 1980. In these techniques, an important element in the success of the treatment is the good positioning of the bracket and of its groove on the tooth, since this positioning determines the orientation of the forces that are imposed on the corresponding tooth and thus the orientation of the tooth in the various spatial directions when it is located in the final corrected position. This positioning is much more difficult to carry out in the lingual technique than in the technique known as labial or vestibular (in which the apparatus is located on the anterior face of the teeth) on account of the great angulation of the posterior faces of the teeth. This angulation means that a small error in the positioning of the bracket can place the groove in an incorrect position which is incapable of correcting the position of the tooth as desired.

IT techniques have been able to bring significant improvements to the ease of designing customized orthodontic apparatuses that are specific to each patient.

In particular, document WO-A-03/068099 teaches designing in a customized manner an assembly formed firstly by the virtual image of a base for fixing to the tooth, designed digitally on the basis of a computer image of the patient's arch with the malpositioned teeth, and secondly by a virtual image of a bracket provided with a groove for the insertion of the orthodontic arch wire, this image being drawn from a virtual library of brackets having predetermined forms. Next, a bracket formed of a single body resulting from the combination of these two images is produced by rapid prototyping. Next, an orthodontic arch wire that is shaped with the aid of a special device and is intended to connect the brackets and to bring the patient's teeth into the corrected position is designed.

Once the orthodontic arch wire has been inserted into the groove in the bracket, this groove is closed off by the practitioner so as to keep the arch wire there. Most commonly, this closing off is realized by inserting a metal or elastomeric ligature into the groove. However, this method has the drawback of not having optimum reliability on account of the fact that it is possible for the ligature not to be fitted correctly by the practitioner and its properties can change over time, in particular in the case of an elastomeric ligature. If the ligature is displaced or damaged, the patient has to go to the orthodontist's practice in order to have it replaced. Likewise, the desired realization of each ligature takes a great deal of time, and this makes the fitting of the arch wire a lengthy and uncomfortable procedure for the patient. Finally, if, during the course of the treatment, it is necessary to change the arch wire, the orthodontist has to irreversibly destroy the ligatures in order to remove the arch wire, this procedure also being lengthy and uncomfortable for the patient. This step of destroying the ligature also causes the orthodontist to exert forces that are transmitted to the bracket and can weaken its connection to the base.

Considerable progress has been made by using what are known as "self-ligating" brackets. These brackets are designed to hold an elastic (metal) clip which, once the arch wire has been inserted, is placed in a position which closes off the groove and allows the clip to prevent the arch wire from coming out. This placement is generally carried out by sliding the clip in the longitudinal direction of the bracket between a stand-by position leaving the groove open for the insertion of the arch wire and a closed functional position closing off the groove, it being possible for this sliding to be complemented by a rotational movement as in document U.S. Pat. No. 6,776,613. The clip is moved manually by the orthodontist using one of his usual tools and takes only a fraction of a second. Similarly, the disengagement of the clip prior to changing the arch wire is carried out by simply pulling in the opposite direction to the previous sliding and is also very quick. Finally, the mechanical and dimensional characteristics of the metal clip are stable over time and if the bracket and the clip are produced with good dimensional precision, the functionality and reliability of the ligature are satisfactory.

In the known self-ligating brackets, the opening of the clip by a translational movement optionally complemented by a rotational movement always requires the formation of a functional zone enabling the closing and opening movements of the clip. Conventionally, this zone is formed in the very body of the bracket, and this brings about a certain number of drawbacks:
the functional zone of the movement means that the base/bracket assembly has to have a thickness that may be considered too great to give the patient optimal comfort;
the functional zone cannot be altered in response to any change in the orientation of the bracket, thereby requiring as many types of brackets as there are possible orientations to be manufactured.

The aim of the invention is to provide orthodontists with a device for connecting a tooth and an orthodontic arch wire, comprising a self-ligating bracket and its associated clip, and limiting or doing away with the abovementioned drawbacks.

To this end, one subject of the invention is an assembly formed by:
- a self-ligating bracket intended to be part of an orthodontic apparatus, said bracket having in its longitudinal direction an outer face and an occlusal face and being provided on its outer face with a groove for holding an orthodontic arch wire;
- an elastic clip that can be moved reversibly between an open position, leaving a free passage for the insertion of the arch wire into the groove or the extraction of the arch wire from the groove, and a closed position closing off the groove;
- and a base having an outer face and an occlusal face, said outer face of the base supporting said bracket and said occlusal face being intended to rest on a patient's tooth by conforming to the surface of said tooth, said base having a support for the bracket;

characterized in that said base helps to guide the clip by engaging with the bracket while said clip is moved between its open position and its closed position.

The clip may be moved between said positions substantially by a rotational movement, without the clip sliding in translation.

The clip may be moved between said positions substantially by a rotational movement, with the clip then sliding in translation or vice versa.

The clip may be moved between said positions substantially by a sliding movement in translation of the clip.

The clip may be generally U-shaped, with a first arm, which closes off the groove in the bracket, being held in a first housing formed on the outer face of the bracket, and with the end of a second arm being held in a housing formed on the occlusal face of the bracket.

The base may then carry on its outer face a wall that delimits, together with the occlusal face of the bracket, a housing in which the end of the second arm of the clip is held.

The clip may have a grasping means enabling the practitioner to move it between said positions.

Said grasping means may be an orifice formed in said first arm of the clip.

Said base may have on its outer face a support on which said bracket is placed.

Said support may comprise said wall delimiting, together with the occlusal face of the bracket, a housing in which the end of the second arm of the clip is held.

The base may be made to measure, for example by rapid prototyping or machining.

The base may be mass produced.

The assembly may be intended for an orthodontic apparatus of the lingual type.

The assembly may be intended for an orthodontic apparatus of the vestibular type.

One subject of the invention is an orthodontic apparatus comprising an orthodontic arch wire and assemblies which each comprise a bracket, a clip and a base that are each intended to be fitted to a patient's tooth, wherein at least one of said assemblies is of the above type.

As will have been understood, the invention is based on a novel design of the assembly formed by a self-ligating bracket, the clip which closes off its groove and the base which supports the bracket. In the invention, the movement of the clip is not guided just by the bracket, but the movement path of the clip is also guided and limited by the base.

It is thus possible to give the bracket a more compact configuration in its longitudinal direction since the guiding function of the clip which is fulfilled in the prior art only by the bracket is in this case fulfilled jointly by the bracket and the base, thereby making it possible to significantly reduce the size of the bracket/base assembly. Even though this shortening can be relatively small, several ¹⁄₁₀ of a mm, for example, it nevertheless provides very appreciable extra comfort for the patient, especially if the apparatus for which the assembly is intended is of the lingual type, as in the preferred (but not exclusive) application example of the invention.

The invention also makes it possible to place the bracket in different orientations without having to alter the form thereof. It is thus the base which adapts the form and the dimensions of the space which are necessary for the opening and closing movements of the clip.

It should be noted that the use of purely rotational opening/closing kinetics of the clip is the most favorable case for implementing the invention since during the rotation the orthodontist has a sufficiently large lever arm to detach layers of tartar that have been able to build up on the bracket and the clip. The difficulties posed by these layers of tartar are regularly cited as being one of the major disadvantages of the most conventional self-ligating brackets in which the movements of the clip comprise a movement in translation in addition to or instead of a rotation.

The invention will be understood better from reading the following description, which is given with reference to the following appended figures, in which.

This description will be given by taking as example a case in which the apparatus for which the bracket-clip-base assembly is intended is an apparatus of the lingual type. However, it will be obvious for a person skilled in the art to transpose the description to an assembly intended for an apparatus of the vestibular type.

Figure 1:
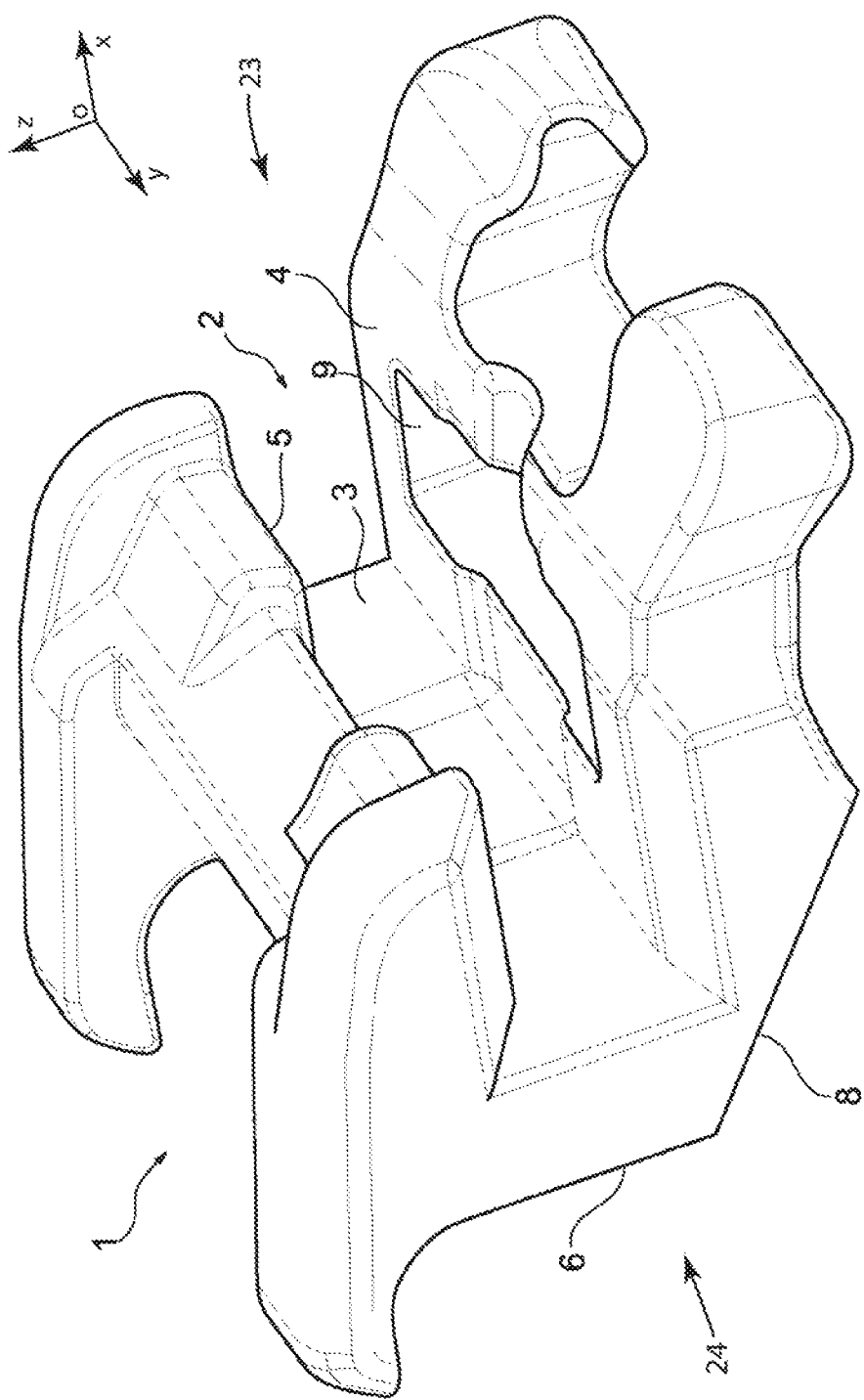
FIGS. 1 and 2 show a perspective view from the front and the rear of an example of a bracket intended for an assembly according to the invention, said assembly being itself intended for an orthodontic apparatus of the lingual type.
Figure 2:
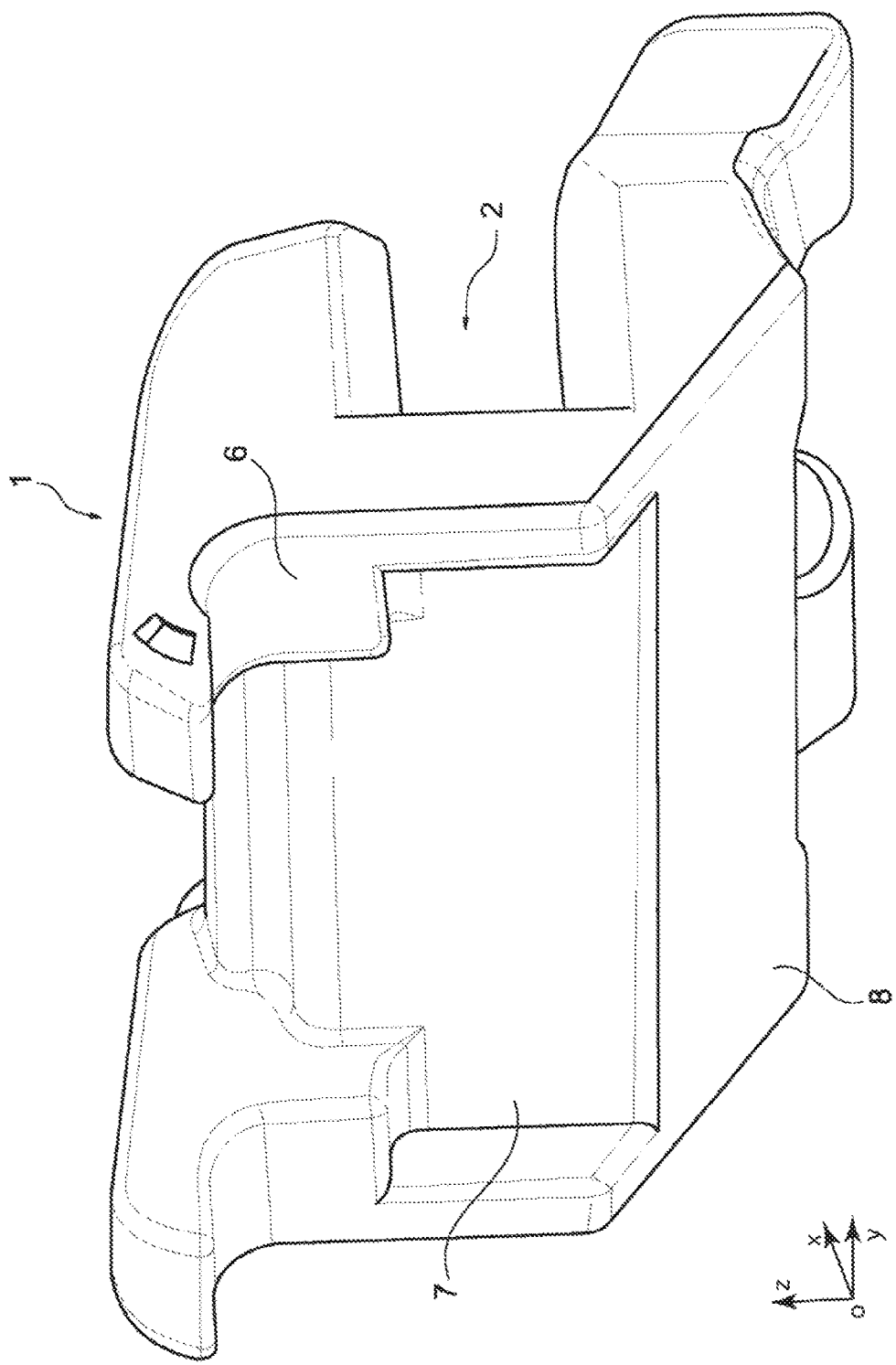

The bracket 1, which is shown in isolation in FIGS. 1 and 2, and of which the precise configuration shown is merely a nonlimiting example, comprises, with reference to the reference frame (O, X, Y, Z) shown in these same figures:

a groove 2 of approximately C-shaped section open in the direction facing toward the patient's mouth (lingual direction), i.e. located on on outer face 23 of the bracket intended to receive an orthodontic arch wire, and delimited by an end wall 3 oriented approximately on the axes OY, i.e. the transverse axis of the bracket 1, and OZ, the axis perpendicular to the longitudinal direction OX of the bracket 1, and by two walls 4, 5 approximately perpendicular to the end wall 3 and forming the two arms of the C. These walls 4, 5 are oriented approximately on the axes OX and OY;

a rear wall 6 situated on an occlusal face 24 of the bracket 1 which is intended to be directed toward the patient's tooth to which the bracket will be fitted, opposite the outer face 23. The rear wall 6 includes a housing 7 which is approximately rectangular in the example shown and the function of which will be seen hereinbelow;

a planar base wall 8 which is intended to rest against the base which will carry the bracket 1.

The wall 4 delimiting the groove 2 and situated closest to the base wall 8 carries a housing 9 which is oriented mainly along the transverse axis OY of the bracket 1, and the function of which will be explained hereinbelow.

Figure 3:
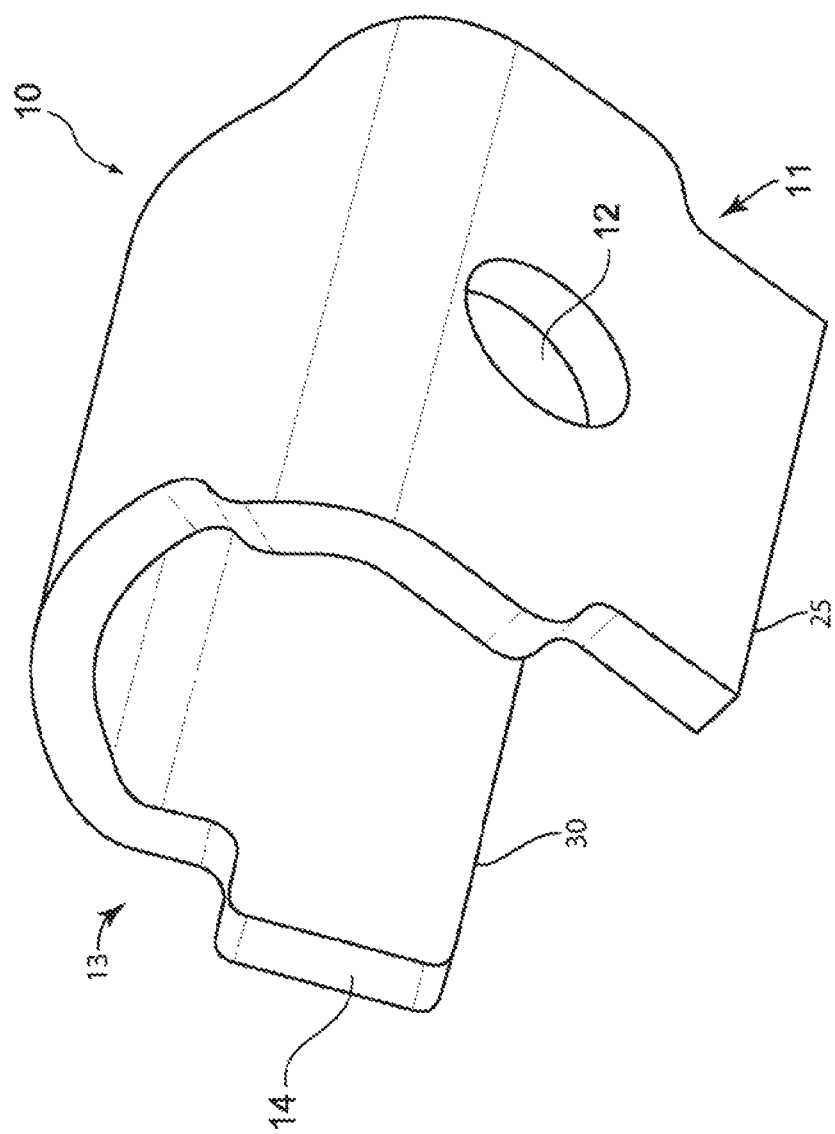
FIG. 3 shows a perspective view of the clip associated with this bracket.

The clip 10, which is shown in isolation in FIG. 3, has elastic properties which enable it to fulfill the functions which will be described below. It is approximately U-shaped, with the arms being, at rest, slightly constricted in the example shown.

A first arm 11 is intended to close off the groove 2 in the bracket 1 when the clip 10 is in place. It preferably carries grasping means that enable the orthodontist to move the clip 10 between its "open" position, releasing the groove 2 for the insertion of the arch wire into the groove 2 or the extraction of the arch wire from the groove 2, and its "closed" position, in which the arch wire is blocked in the groove 2 by the clip 10. In the example shown, these grasping means are an orifice 12 into which the orthodontist can introduce the end of a tool that forms a lever. The end 25 of the first arm 11 is intended to be inserted into the housing 9 in the wall 4 of the bracket 1. The wall 4 delimits the groove 2 and is situated closest to the base wall 8.

A second arm 13 carries at its end a tab 14 intended to be inserted into the housing 7 formed on the rear wall 6 of the bracket 1. This tab 14 and the housing 7 have approximately complementary forms so that the housing 7 can hold the tab 14 in the transverse direction OY.

Figure 4:
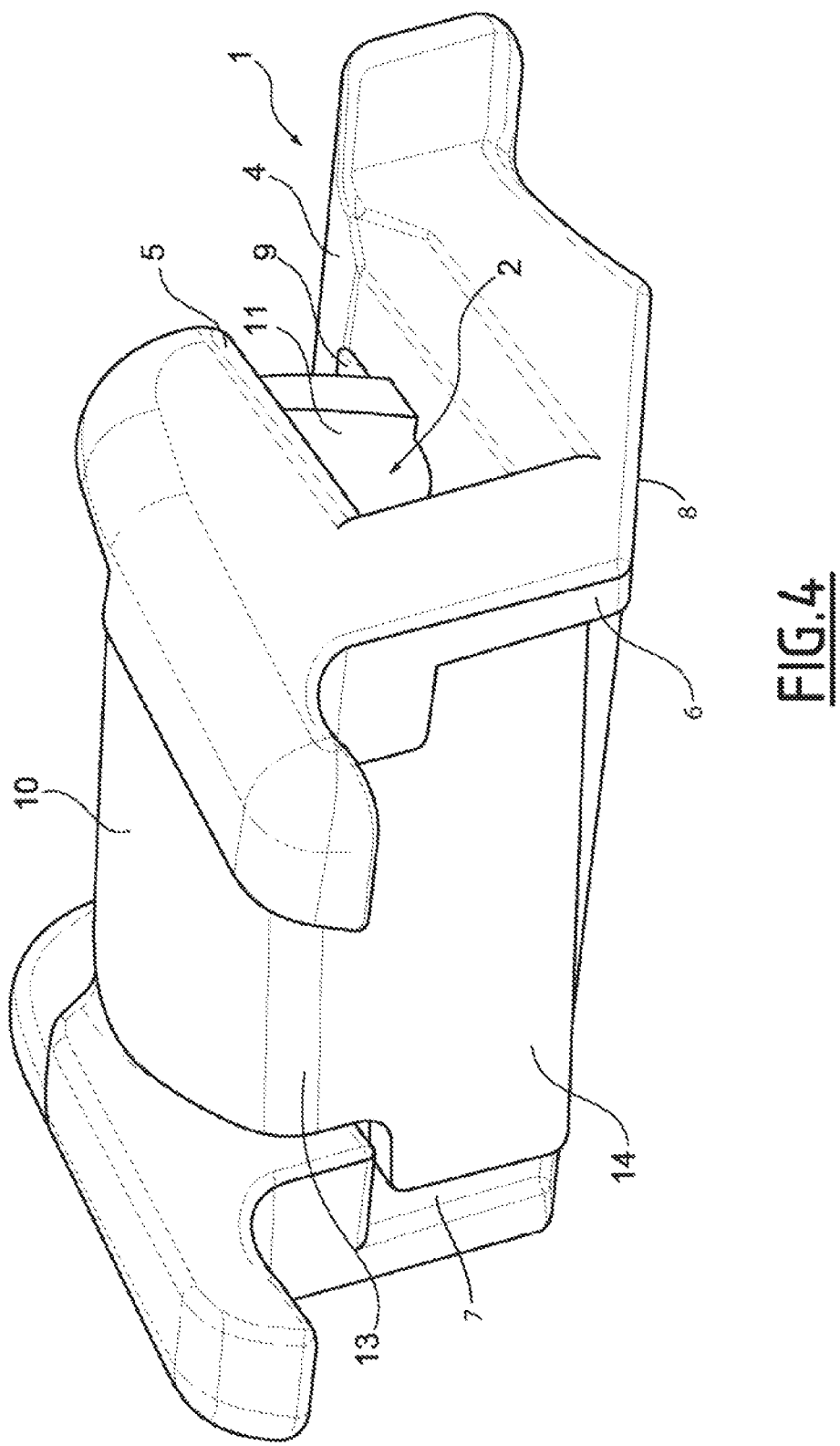
FIG. 4 shows the clip placed on the bracket.

FIG. 4 shows the bracket 1 with the clip 10 fitted to it. The ends 25, 30 of the arms 11, 13 of the clip 10 are inserted in their respective housings 9, 7 and the clip 10 overlaps the wall 5 of the bracket 1 delimiting the groove 2 furthest away from the base wall 8.

The bracket 1 can be manufactured from any conventional material suitable for this use, such as a biocompatible metal material (stainless steel, titanium, ceramic in particular) and by any conventional method that provides the excellent dimensional precision necessary for self-ligating brackets. Machining or laser cutting are particularly recommended, more than rapid prototyping.

Figure 5:
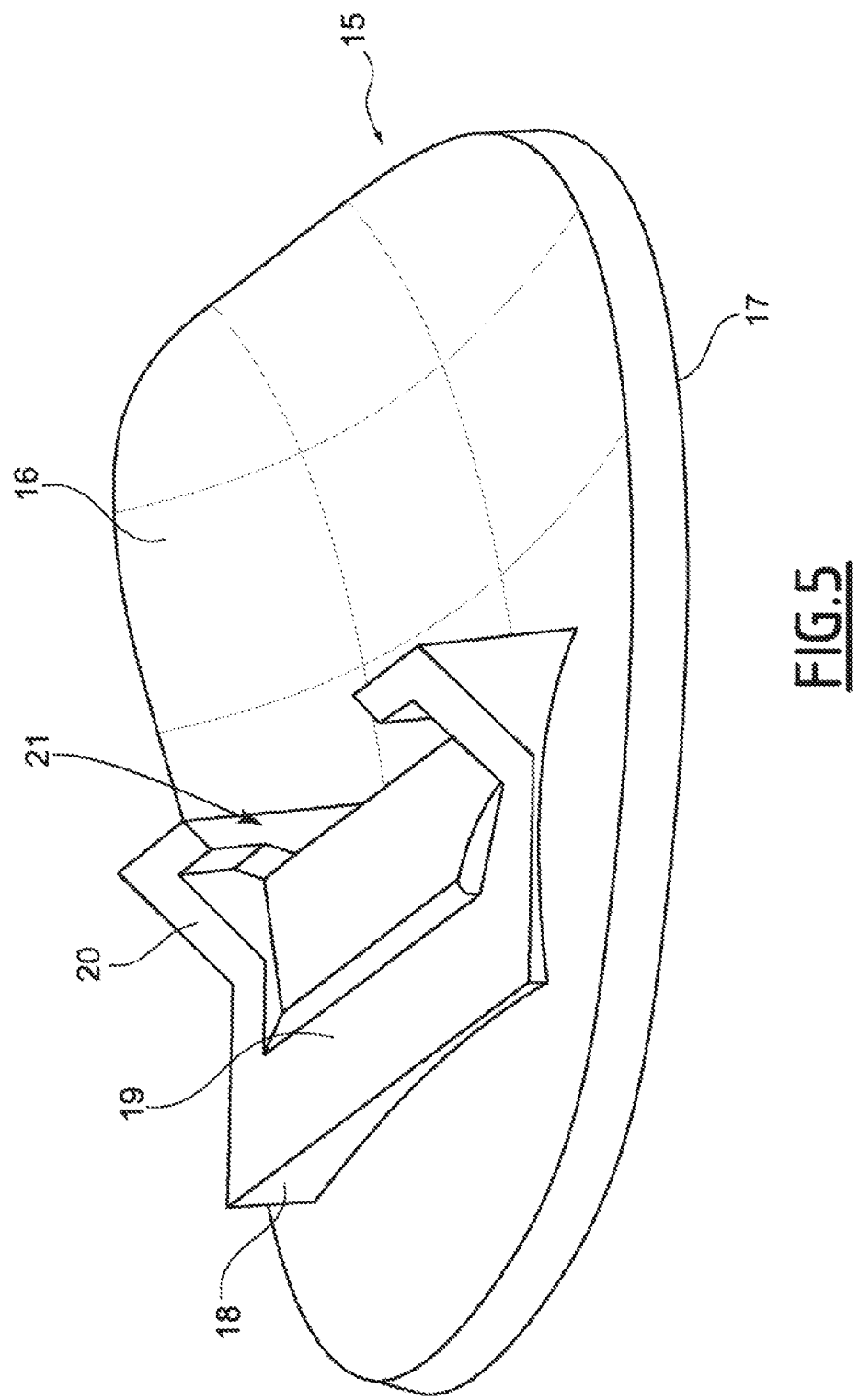
FIGS. 5 and 6 show a perspective view from the front and the rear of the base, on which the bracket is intended to be placed.
Figure 6:
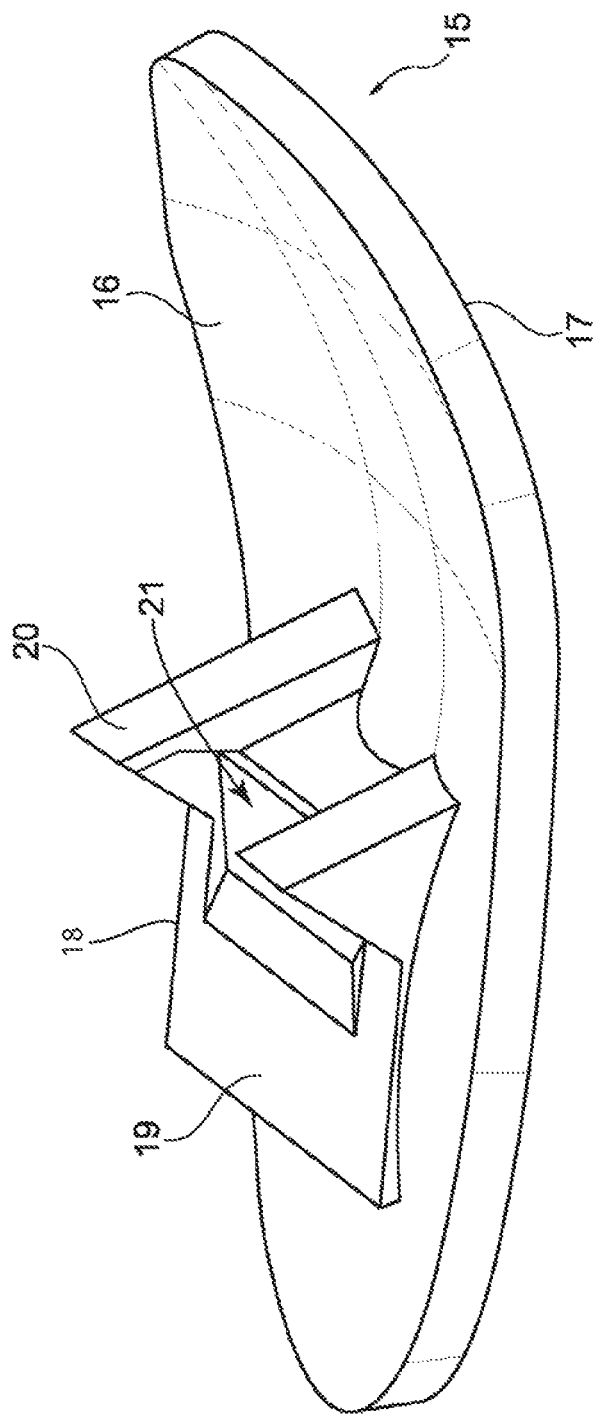

FIGS. 5 and 6 show the outer (upper) face 16 of the base 15 of which the bracket 1 is intended to be fitted. The occlusal (lower) face 17 of the base 15 is intended to be placed on the corresponding tooth of the patient by being conventionally fixed thereto by means of an adhesive material. In the example shown, the upper face 16 of the base 15 carries a support 18 for the bracket 1. This support 18 comprises a planar part 19 and an abutment 20. The planar part 19 can optionally comprise a housing, in which the bracket 1 is intended to be placed. Such a housing promotes the precision of placement of the bracket 1 and contributes to keeping it securely in position. It also reduces the overall thickness of the assembly for one and the same configuration of the bracket 1, thus providing the patient with additional comfort.

According to the invention, on that face of the abutment 20 which is intended to face away from the bracket 1, the support 18 also comprises a housing 21 into which the tab 14 of the clip 10 is intended to be inserted when the clip 10 is in the position closing off the groove 2. This housing, together with the housing 7 of the bracket 1, delimits the space into which the tab 14 of the second arm 13 of the clip 10 moves while the clip 10 moves during an opening or closing operation of the groove 2.

The base 15 can be manufactured by any method suitable for the required precision and for the materials used, which are conventional materials for manufacturing bases. Rapid prototyping or machining are preferred but not exclusive examples thereof.

Figure 7:
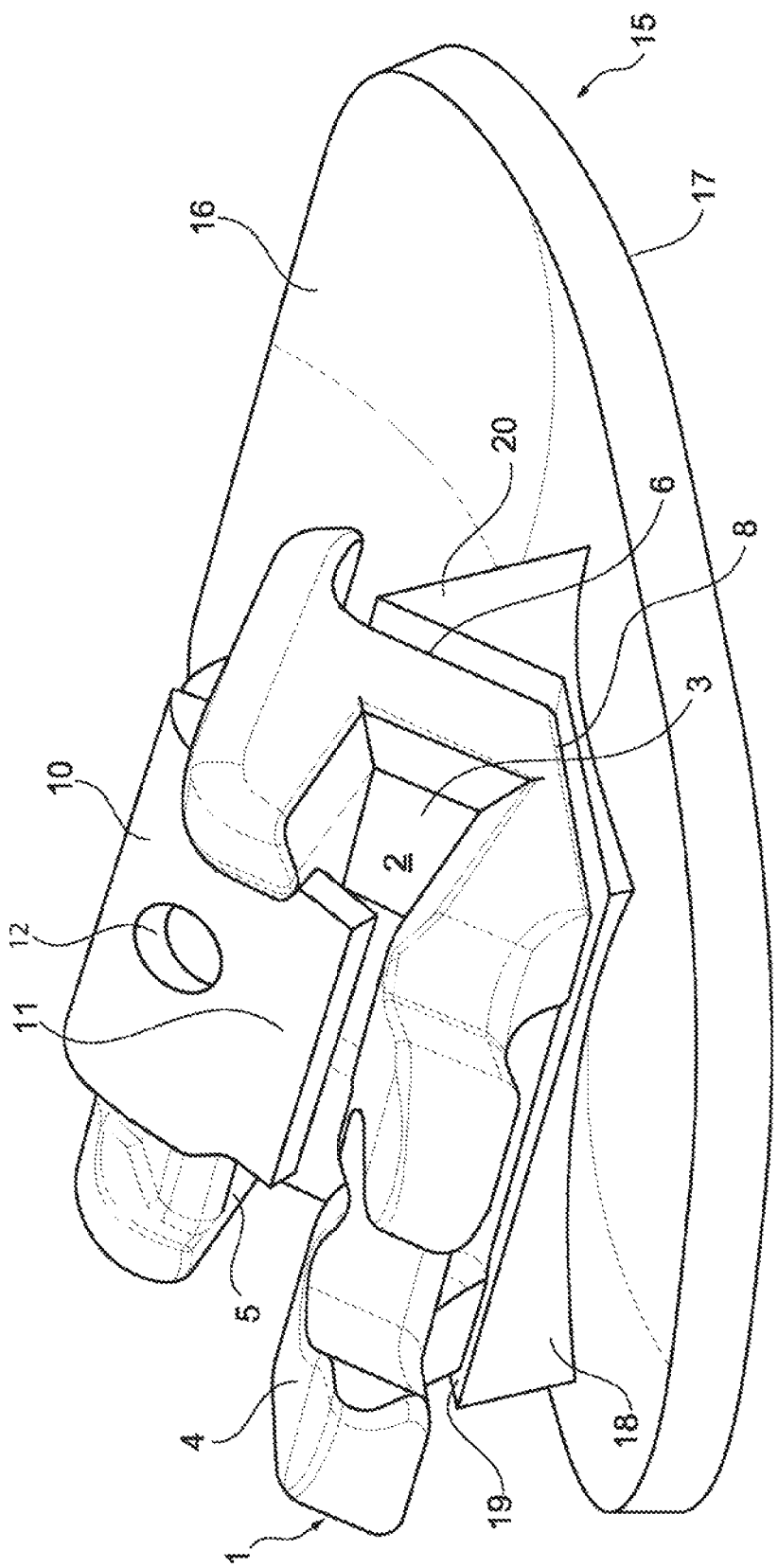
FIG. 7 shows a perspective view from the front of an example of the assembly according to the invention, which is formed by the bracket, the clip and the base from the preceding figures, with the clip in the open position.

FIG. 7 shows the bracket 1/clip 10/base 15 assembly fitted with the clip 10 in the open position, thus making it possible to insert the orthodontic arch wire into the groove 2 of the bracket 1 or to extract it therefrom. In this position, the lower edge 23 of the tab 14 (not visible in FIG. 7, see e.g. FIGS. 9 and 10) is against the wall of the housing 7 on the rear wall 6 of the bracket 1, the rest of the tab 14 being spaced apart from the wall 6 but prevented from moving away therefrom by the walls of the housing 21 of the abutment 20 carried by the base 15. The clip 10 is thus guided in rotation as it is moved during the opening or closing of the groove 2.

Figure 8:
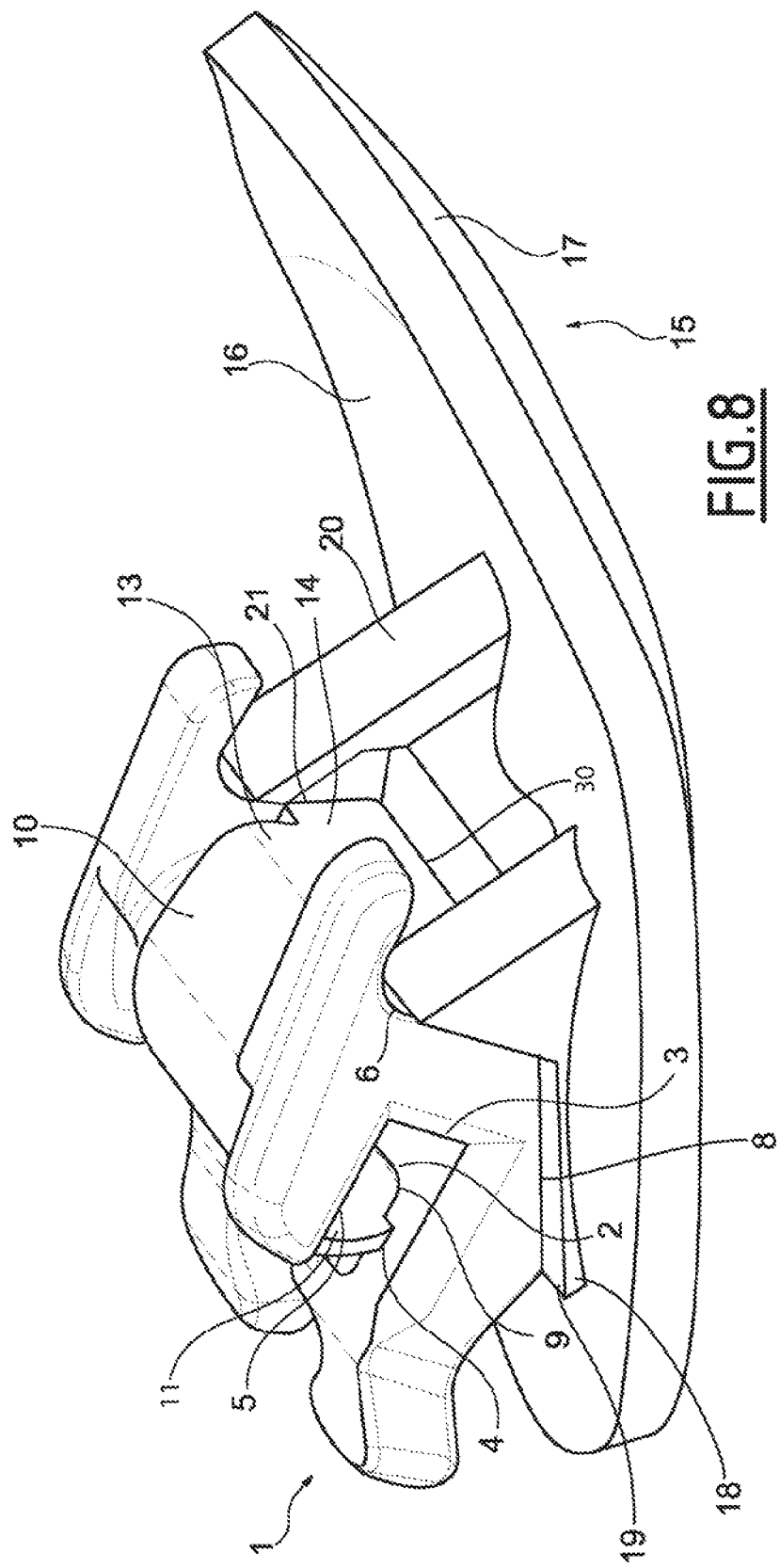
FIG. 8 shows a perspective view from the rear of the assembly formed by the bracket, the clip and the base from the preceding figures, with the clip in the closed position.

FIG. 8 shows a view in the opposite direction to that in FIG. 7 of the bracket 1/clip 10/base 15 assembly fitted with the clip 10 in the closed position, thus blocking the orthodontic arch wire in the groove 2 in the bracket 1. It can be seen that in this position, the tab 14 of the clip 10 is pressed against the rear wall 6 of the bracket 1 and is thus contained inside the housing 7. For its part, the end of the first arm 11 of the clip 10 has been placed by the orthodontist, by a rotational movement, in the corresponding housing 9 of the bracket 1. This rotational movement is easy and very quick to carry out. In particular, it is not prevented by any build-up of tartar on the assembly because the lever arm produced by the form of the clip 10 and its rotation are sufficient to destroy or detach this build-up, whereas a translational movement would tend to be considerably hampered by a build-up of tartar on the track of the clip.

The clip 10 has sufficient elasticity to keep the end 25 of the first arm 11 and the tab 14 at the end 30 of the second arm 13 in their respective housings 9, 7. The orthodontic arch wire only being able to exert forces on the clip 10 in the direction of removal of the arch wire from the groove 2 (axis OX) since these forces are channeled by the walls 4, 5 of the groove 2 and thus do not tend to remove the clip 10 from its housings 7, 9.

Figure 9:
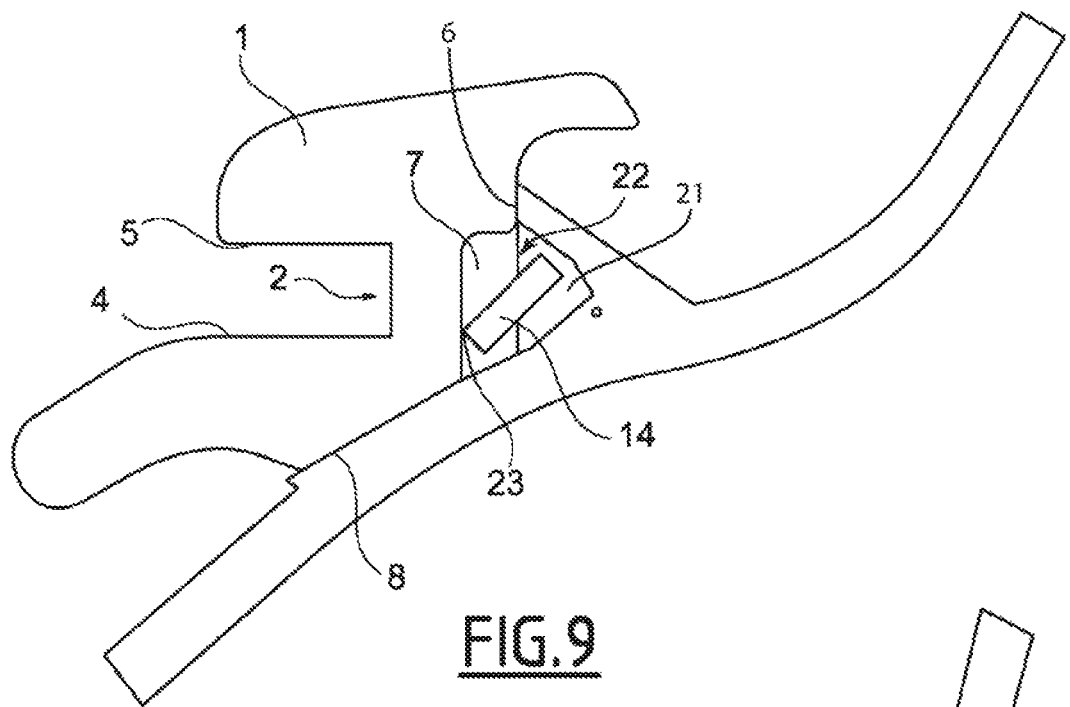
FIG. 9 shows a profile view in section of the assembly formed by the bracket, the clip and the base from the preceding figures, with the clip in the open position.
Figure 10:
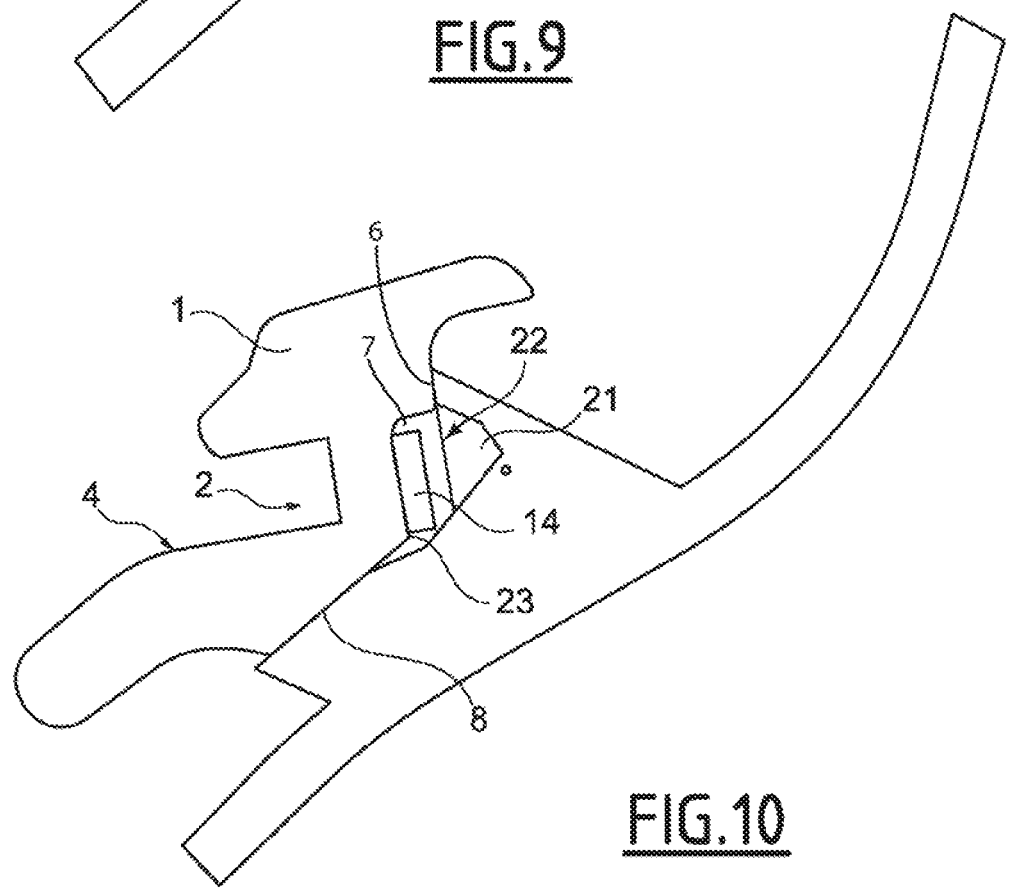
FIG. 10 shows a profile view in section of the assembly formed by the bracket, the clip and the base from the preceding figures, with the clip in the closed position.

FIGS. 9 and 10 show profile views in section of the assembly according to the invention shown in the preceding figures. In FIG. 9, the clip 10 is in the open position and in FIG. 10, the clip 10 is in the closed position. The section plane passes close to a lateral edge of the bracket 1 and consequently, of all the portions of the clip 10, only the tab 14 is visible in these sections. However, these sections clearly reveal how the tab 14 is contained in the housing 22 formed by the combination of the housing 7 formed on the bracket 1 and the housing 21 formed on the support 18. The dimensions of the housing 22 are calculated such that the tab 14 can move very approximately in rotation, its lower edge 23 being able to bear against the wall of the housing 7 formed on the bracket 1 by being prevented from moving away from its rotational path by the wall of the housing 21 formed on the support 18. This rotation is thus carried out in a completely guided manner when performed by the orthodontist, without it being necessary to realize an axis that would pass through the bracket 1 and the clip 10. This makes it possible to preserve a design for the components of the assembly that is not excessively complex and is compatible with the degree of miniaturization of the components.

The specific example that has been described is not limiting. In particular, the base can be designed to help guide the clip in a direction other than a simple rotation: a rotation complemented by sliding in translation or vice versa, or simply sliding in translation.

In the most favorable case, the base is made to measure and manufactured by methods such as rapid prototyping or machining. Alternatively, it may be acceptable to mass produce the base.

The invention claimed is:

1. An orthodontic assembly, comprising:
   a bracket comprising a first wall, a second wall, and a base wall, the first wall being generally opposite the second wall, a groove configured to receive an archwire therein extending into the bracket between the first and second walls generally towards the base wall;
   a clip having a first arm with a first end and a second arm with a second end and the clip is movable relative to the bracket between an open position wherein the groove is open and a closed position wherein the first arm of the clip occludes the groove;
   a base comprising a lower face configured to engage a tooth of a patient and an upper face, the upper face opposite the lower face; and
   a support secured to the upper face, the support comprising a planar portion and an abutment, the bracket secured to the support with the base wall secured to the planar portion and the second wall secured to the abutment to position the bracket relative to the base.

2. The orthodontic assembly of claim 1, wherein the abutment further comprises a first housing extending into the abutment in a direction away from the second wall of the bracket, the second end of the clip being movable within the first housing between the open position and the closed position of the clip.

3. The orthodontic assembly of claim 2, wherein the first housing is further delimited by the second wall of the bracket.

4. The orthodontic assembly of claim 2, wherein the clip is at least translationally movable within at least the first housing.

5. The orthodontic assembly of claim 2, wherein the clip is at least rotationally movably within at least the first housing.

6. The orthodontic assembly of claim 2, wherein the first housing in the abutment at least partially defines a movement of the clip between the open position and the closed position.

7. The orthodontic assembly of claim 2, further comprising a second housing extending into the bracket from the second wall, the second housing forms a combined housing with the first housing when the bracket is secured to the support, and the second end of the second arm being movable within the combined housing between the open position and the closed position of the clip.

8. The orthodontic assembly of claim 7, wherein the second arm comprises a tab at the second end of the second arm, the tab being of a comparatively greater width than a remaining portion of the second arm, the tab being movably secured within the combined housing.

9. The orthodontic assembly of claim 8, wherein the tab is rotatable within the combined housing and a wall of the abutment prevents translative movement of the tab relative to the bracket.

10. The orthodontic assembly of claim 8, wherein the clip rotates between the open position and the closed position about a lower edge of the tab within the combined housing.

11. The orthodontic assembly of claim 8, wherein when the clip is in the closed position, the tab of the second arm of the clip is secured within the second housing.

12. The orthodontic assembly of claim 7, wherein a movement of the clip between the open position and the closed position includes at least one of a rotation and a translation and the combined housing defines the movement of the clip.

13. The orthodontic assembly of claim 2, further comprising a clip housing extending into the first wall from the groove, wherein when the clip is in the closed position, the first end of the first arm is inserted into the clip housing and when the clip is in the open position, the first end of the first arm is free from the clip housing.

14. The orthodontic assembly of claim 1, wherein the bracket further comprises a third wall and an end wall intermediate the first wall and the second wall, the groove being defined by the first wall, the third wall, and the end wall.

15. The orthodontic assembly of claim 14 wherein a second housing extends into the bracket to a position below the end wall in a direction in alignment with the groove.

16. The orthodontic assembly of claim 14, wherein the first wall extends past the third wall and the first arm of the clip moves over the third wall between the open and closed positions.

17. The orthodontic assembly of claim 1, wherein the planar portion and the abutment of the support define an orientation of the bracket relative to the base.

18. The orthodontic assembly of claim 1, wherein the lower face is configured to rest on a patient's tooth by conforming to the surface of said tooth.

19. The orthodontic assembly of claim 18, wherein the bracket is adapted to be positioned at a predetermined treatment position on said tooth by the conforming of the lower face to the surface of said tooth and the orientation of the bracket relative to the base defined by the support.

* * * * *